United States Patent [19]  [11]  4,267,339
Tedeschi  [45]  May 12, 1981

[54] IMIDAZO(2,1-B)THIAZOLES

[75] Inventor: Enzo Tedeschi, Tel-Aviv, Israel

[73] Assignee: Plantex Ltd., Netanya, Israel

[21] Appl. No.: 755,031

[22] Filed: Dec. 28, 1976

Related U.S. Application Data

[63] Continuation of Ser. No. 546,442, Feb. 3, 1975, abandoned.

[30] Foreign Application Priority Data

Feb. 7, 1974 [IL] Israel ......................................... 44161
Jun. 26, 1974 [IL] Israel ......................................... 45127

[51] Int. Cl.$^3$ .................... A61K 31/425; C07D 513/04
[52] U.S. Cl. ..................................... 548/154; 548/155; 548/337; 548/339; 548/340; 546/271; 424/263; 424/270
[58] Field of Search .................. 260/306.7 T; 548/154

[56] References Cited

FOREIGN PATENT DOCUMENTS 1445669 3/1969 Fed. Rep. of Germany .... 260/306.7 T

OTHER PUBLICATIONS

Ochiai et al., Chem. Abstracts, vol. 32, col. 4161 (1938).
Matsukawa et al., Chem. Abstracts, vol. 46, col. 8094 (1952).
Pyl et al., Chem. Abstracts, vol. 58, cols. 2443-2444 (1963).
Kochergin, Chem. Abstracts, vol. 55, col. 1586 (1961).
Mazur et al., Chem. Abstracts, vol. 73, Abstract No. 66501c (1970).
Anisimova et al., Chem. Abstracts, vol. 81, Abstract No. 104,149u (1974).
Almirante et al., J. Med. Chem., vol. 9, pp. 29-33 (1966).
Paolini et al., J. Med. Chem., vol. 12, pp. 1031-1034 (1969).

*Primary Examiner*—Alton D. Rollins
*Attorney, Agent, or Firm*—Hubbell, Cohen, Stiefel & Gross

[57] ABSTRACT

There are disclosed certain novel imidazo(2,1-b)thiazoles, their physiologically acceptable acid addition—or quaternary ammonium salts and a process for their preparation. Said compounds show a good antidiabetic activity.

27 Claims, No Drawings

IMIDAZO(2,1-b)THIAZOLES

This is a continuation, of application Ser. No. 546,442, filed Feb. 3, 1975, abandoned.

The present invention relates to new imidazo(2,1-b)thiazoles, processes for their preparation and pharmaceutical compositions containing said compounds.

Several orally administrable hypoglycaemic drugs are known which belong mainly to the following chemical groups:

(1) Arylsulfonylurea derivatives. This group comprises well known drugs, e.g. Tolbutamide, Chlorpropamide, Dibenclamide, Acetoxamide, Acetoxamide and Tolazamide.

(2) Biguanide derivatives, e.g. Phenformin

The arylsulfonylureas reduce the fasting blood sugar level of intact or glucose loaded animals, but they do not act in this manner in animals made severely diabetic with alloxane. In human beings the arylsulphonylureas are effective only in individuals who have a pancreatic reserve of insuline as in non-diabetics or mild diabetics whose illness started in adult life, requiring a daily insuline dosage below 10 units. However, these compounds do not act in patients with severe diabetes and in cases of juvenile or growth onset type of diabetes. Moreover, they can not be used in patients with a tendency to ketosis or ketoacidosis. They may cause severe hypoglycaemia, with the acute neurologic picture of hemiparesis and coma. These compounds do not possess a direct insuline-like activity.

Phenformin and certain other biguanides are more effective than the arylsulfonylurea as they produce hypoglycaemia also in pancreatectomized or in severe alloxane-induced diabetes. The optimal decreasing of blood glucose concentration (Δ mean=135), is achieved with Phenformin in animals with a starting blood glucose concentration of 250-300 mg/100 ml. However, some activity (Δ mean=90) is still achieved at a starting concentration up to 380 mg/100 ml. However, the therapeutic dose of Phenformin is close to the toxic one in human beings and may produce anorexia, nausea, vomiting, and later weakness, lethargy and weight losses.

The Phenformin combined with insuline may make a labile diabetic patient more stable and this is one of the main clinical applications. Other applications are in cases of maturity onset diabetes accompanied by obesity or primary and secondary aryl sulfonylureas failures.

There was therefore the need for a new, non-toxic anti-diabetic drug, with an insuline-like mechanism of action, acting orally on the most severe diabetes as for example for juvenile or growth onset type of diabetes.

It has now surprisingly been found that certain imidazo (2,1-b)thiazoles achieve improved properties over the known drugs.

Some of the compounds according to the present invention have a mean, statistic antihyperglycaemic activity which is stronger that that of Phenformin and they are particularly effective in the treatment of severe diabetes on rats. When the starting blood glucose concentration is higher than 380 mg/100 ml the Δ can reach a mean value of more than 230 with a Δ% of 55%. In equal conditions the mean Δ and Δ% of the Phenformin are respectively 50 and 10%. The lasting time of activity is longer than that of Phenformin (5 hours) and it is still active after 24 hours. No glycosuria, antidiuretic or other activities are present as undesirable or toxic side effects. The hypoglycaemic effect of the new imidazo (2,1-b)thiazoles derivative on normal beings is, as with Phenformin, very low (Δ 20%) thus preventing a possible hypoglycaemic coma.

The present invention thus consists in imidazo-(2,1-b)thiazoles of general formula I

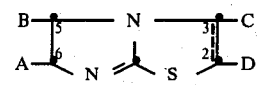

wherein at least one of the substituents A, B, C and D stands for one of the following radicals: $(CH_2)_n COOR$, $(CH_2)_n CON<$, $(CH_2)_n CN$, $(CH_2)_n CF_3$, $(CH_2)_n CH_2X$, $(CH_2)_n CH_2OCOR^1$, $(CH_2)_n COR^1$, in which:

n is an integer of 0-2,

R stands for a (straight or branched) alkyl, aryl aralkyl or alicyclic radical, for a hydrogen atom, for an inorganic cation e.g. sodium and calcium or for an ion

in which E, E' and E'' may stand for hydrogen or for the same or different hydroxyalkyl, alkyl, alkylamino (optionally substituted), alkylcarbalkoxy or alkylcarboxy radical;

the N< group standing for an unsubstituted or substituted amine, cyclic amine or a hydroxylamine or hydrazine group;

X stands for a halogen atom, or for a hydroxy, mercapto, alkoxy, aryloxy or aralkoxy radical, or for a N< group;

$R^1$ stands for (straight or branched) alkyl, aryl, aralkyl or heterocyclic radical;

substituents A, B, C and D not standing for one of the above groups standing for a hydrogen atom or for a (straight or branched) alkyl, aryl, aralkyl or heterocyclic radical;

C and D together with the bond connecting them may stand for a cycloaliphatic radical;

the dotted line standing either for two hydrogen atoms or for a C═C bond;

or one of the physiologically acceptable acid addition - or quaternary ammonium salts; excluding:

a. 2-Carbomethyl-3,5-dimethyl-6-carboethoxyimidazo(2,1-b)thiazole; and b. 3,5-dimethyl-6-carboethoxy-imidazo(2,1-b)thiazole.

Preferred compounds of general formula I are compounds of general formula Ia

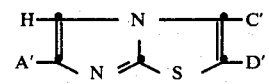

in which
A' stands for COOR'', R'' standing for a hydrogen atom for a hydroxyalkylammonium or an inorganic cation or for a lower alkyl group; or for $CH_2OCOR'''$, R''' standing for an alkyl group or for an optionally substituted phenyl group;

C' stands for methyl, tert. butyl or an optionally substituted phenyl group; and D' stands for hydrogen or an alkyl group.

The alkyl radical has advantageously 1–8 carbon atoms, the aryl radical is preferably a substituted or unsubstituted phenyl, diphenyl or naphthyl radical. The heterocyclic radical is preferably selected among the substituted or unsubstituted imidazolyl, pyridyl, thienyl, or furyl radicals.

As suitable acids for the preparation of the acid addition salts there should be mentioned the hydrochloric, hydrobromic, nitric, sulfuric and phosphoric acid. Moreover, also certain organic acids may be utilised. As preferable esters for the preparation of the quaternary ammonium salts there may be mentioned esters of sulphuric, hydrochloric, hydrobromic and of certain aromatic sulfuric acids.

The above two excluded compounds have been described by Ochiai, Ber. 69, 1650 (1936). However, no pharmaceutical activity has so far been reported for same.

The compounds of general formula I can be prepared by various processes.

One process for the preparation of compounds of general formula I consists in the condensation of an α-halocarbonyl derivative of general formula II

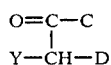

in which C and D have the same meaning as above, Y stands for a halogen atom and the carbonyl group may be protected by a readily cleaved group; with a 2-mercaptoimidazole derivative of general formula III

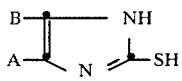

in which A and B have the same meaning as above to yield a thiocarbonyl derivative of general formula IV

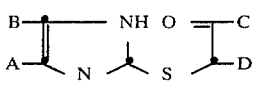

in which A, B, C and D have the same meaning as above and, if the carbonyl compound of the halocarbonyl derivative of general formula II was protected, subjecting the compound obtained to an acidic cleavage reaction; said thiocarbonyl derivative of general formula IV being converted into the compound of general formula I with a suitable reagent by cyclisation and dehydration by methods known per se.

The condensation reaction between the compounds of general formulae II and III is preferably performed in a suitable inert solvent. As suitable solvents there may be mentioned, for example, alcohols, e.g. methanol, ethanol, isopropanol, butanol, or aprotic solvents, e.g. acetonitrile, dimethylformamide (DMF), dimethylsulfoxide (DMSO), etc.

The condensation reaction is performed at temperatures, which vary between room temperature and the boiling temperature of the solvent.

The reaction can be performed in any suitable medium, i.e., in an alkaline, neutral or acidic medium. In case that the reaction is performed in an alkaline medium a metal hydride or an alkoxide are used and the main reaction product is the thiocarbonyl derivative of general formula IV. When the reaction is performed in a neutral medium at room temperature, the main reaction product is the corresponding hydrohalide salt of the thiocarbonyl derivative of general formula IV. However, in case that said condensation reaction is performed in a neutral medium at elevated temperatures, e.g. 80°–150° C., the ring closure and the dehydratation of the thiocarbonyl derivative of general formula IV is directly performed and the desired compound of general formula I is obtained.

The thiocarbonyl derivative of general formula IV is, as stated above, not always isolated. In some instances the final compound of general formula I is directly obtained. Sometimes the ring is closed but the dehydratation reaction has to be performed. In case that an intermediate compound is isolated the ring closure and/or the dehydratation reaction can be performed by various methods. By a preferred method the base of said thiocarbonyl derivative of general formula IV or the hydroxy dihydro thiazole derivative is refluxed in phosphorus oxychloride or sulfuric acid. Another method consists in refluxing a hydrohalic salt of said thiocarbonyl derivative is a suitable inert solvent, e.g. butanol.

The reaction time of the ring closure and dehydratation process may vary to a large extent, i.e., between 10 minutes up to 24 hours according to the substituents and the reaction conditions.

The thiocarbonyl derivatives of general formula IV with the exception of 2-thioacetonyl-4(5)-carboethoxy-5(4)-methylimidazole are new compounds. The present invention thus embraces also said new compounds.

Another process for the preparation of compounds of general formula I consists in the condensation of an α-halocarbonyl derivative of general formula V

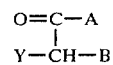

in which A and B have the same meaning as above and Y stands for a halogen atom; with a 2-amino-thiazole derivative of general formula VI

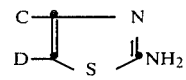

in which C and D have the same meaning as above.

Said condensation reaction is preferably performed in a suitable inert solvent, for example, certain alcohols, aprotic solvents, e.g. methanol, ethanol, acetonitrile, DMF, DMSO, etc. The reaction temperature varies from 0°–150° C. The reaction time varies between some minutes and some days according to the substituents and the reaction conditions.

Most of the compounds of general formula II, III, V and VI, are known. Those which are new ones can easily be prepared by methods analogous to those by which the known compounds are prepared.

The various substituents in the compounds of general formula I may be introduced either directly in the course of one of the above processes or by way of converting one compound of general formula I into another one by methods known per se.

Thus, for example, the COOR, CF₃, and COR' radicals can be introduced in the course of the condensation reaction. The $CH_2X$, $CH_2OCOR'$, CN and CON substituents are better introduced by transformation of the carbalkoxy function, e.g. by reduction to hydroxymethyl, halogenation to chloromethyl and aminolysis of same with a primary, secondary or cyclic amine (X=OH, Cl, N, respectively); esterification with a suitable acid chloride of the hydroxy methyl function (X=CH$_2$OCOR$^1$). The reaction of the chloromethyl derivatives with a suitable metal alkoxide or phenate yields the desired ether (X=CH$_2$OR). The amide group (X=CON) can be obtained directly from the ester or via the acid chloride and from the amide the cyano group can be obtained.

These compounds of general formula I, wherein the dotted line stands for 2 hydrogen atoms can be prepared by reducing a thiocarbonyl derivative of general formula IV with sodium borhydride to yield a -thioalcohol of general formula VII

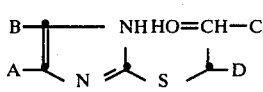

in which A, B, C and D have the same meaning as above and cyclisation and dehydration of the same directly or after esterification.

The β-thioalcohols of general formula I and their esters are new compounds. The present invention embraces also said new compounds.

Those compounds of general formula Ia in which at least one of the substituents A, B, C and D stands for (CH$_2$)$_n$ COOR in which R stands for an inorganic cation e.g. sodium and calcium or for an ion

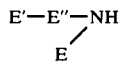

in which E, E' and E" may stand for hydrogen or for the same or different hydroxyalkyl, alkyl, alkylamino (optionally substituted), alkylcarbalkoxy or alkylcarboxy radical; are prepared by dissolving the corresponding imidazo-(2,1-b) thiazole carboxylic acid in an inert solvent and adding to the solution obtained a solution of the appropriate base.

As suitable solvents there may be mentioned, for example, ethanol, acetonitrile, etc.

The acid addition salts of the compounds of general formula I are obtained by methods known per se, e.g. by dissolving the base in a suitable solvent (e.g. alcohols, ethyl acetate, acetonitrile, etc.) and thereafter adding the selected acid at a temperature of 0°–80° until the pH is 1–5.

The quaternary ammonium salts of the compounds of general formula I can also be prepared by methods known per se, for example, by reacting the base with a suitable ester of the desired acid, e.g. butyl bromide, methyl sulphate, methyl p-toluensulphonate, etc. in or without a suitable solvent.

The present invention consists also in pharmaceutical compositions containing as active substance an imidazo (2,1-b) thiazole of general formula I. The new compositions are preferably administered per os. However, if desired, they may be administered in any other suitable form, e.g. as injection, suppositorium, etc.

The new compositions according to the present invention are thus advantageously prescribed in the form of tablets, pellets, capsules, ampoules, powders, granules, solutions, suspensions, emulsions, injections, suppositoriums, etc. Said compositions are prepared in a conventional manner, i.e., by the addition of suitable binders, extenders, carriers, fillers, solvents, emulsifiers, other suitable therapeutic compounds, etc.

Naturally said compositions should comprise therapeutical effective doses of the new compound according to the present invention. Said doses may vary, however one may consider as an effective antidiabetic dose, daily doses from 10 mg up to 3 g of the new compound according to the present invention. Said doses vary according to the compound utilised, to the severeness of the illness, whether the drug is to be administered to a child or to a grown up person and in which manner it is administered.

The present invention consists also in a method for the reduction of the blood sugar level in patients suffering from diabetes in which a composition comprising a therapeutical effective dose of a compound according to general formula I is administered.

The present invention will now be illustrated with reference to the following Examples without being limited by them. All temperatures are given in degrees Centigrade. All melting points are uncorrected. The solvents indicated in brackets after the melting points are those from which the substances are recrystallized.

EXAMPLE 1

158 g of 2-mercapto-4(5)-carbomethoxy imidazole, [(prepared as described in JACS 71, 644–647(1949)], are suspended in 1.5 l of dry methanol containing 1 M sodium methoxide and 169 g of bromoacetaldehyde dimethyl acetale are then slowly added to said suspension. After refluxing the suspension for 16 hours, 1.5 l of benzene are added thereto and the methanol is evaporated. 2-[4(5)-carbomethoxy imidazolyl]thioacetaldehyde dimethyl acetal precipitates; after extraction with isopropanol of the precipitate and evaporation of the solvent 228 g of substance are obtained. Said substance is dissolved in 1.2 l of a 15% aqueous HCl solution and after agitation for 2 hours at room temperature sodium bicarbonate is added until the pH is 7.5. The precipitate obtained is filtered off to yield 149 g of 3-hydroxy-6-carbomethoxy imidazo (2,1-b)-2,3-dihydro thiazole.

The above substance is refluxed for 2 hours in 1.4 l of phosphorus oxychloride. The solvent is distilled off under vacuum; water and chloroform are then added to the residue and sodium bicarbonate is added until pH 7.5 is obtained. The chloroform layer is washed with water and the water phase is extracted with chloroform. The dried chloroform solution is evaporated and the residue is crystallized to yield 84 g of 6-carbomethoxy-imidazo-(2,1-b)thiazole; m.p. 153°–156°, (Abs. ethanol).

EXAMPLE 2

The 6-carbomethoxy imidazo (2,1-b)thiazole prepared as described in Example 1 and a solution of isopropanol containing dry HCl is added until pH2 is obtained after dissolution of the substance. The solvent is evaporated and the residue being 6-carbomethoxy-imidazo-(2,1-b) thiazole HCl is crystallized from absolute alcohol; m.p. 182°–185°.

EXAMPLE 3

A solution of 15 g of 2-aminothiazole and 31.4 g of ethyl-bromo acetoacetate in 200 ml of acetonitrile is stirred for 2 hours at room temperature. After refluxing the solution for 3 hours, it is decolorized and the solvent is evaporated under vacuum. The residue obtained is dissolved in water, then neutralized with sodium bicarbonate and extracted with chloroform. The solvent is dried and evaporated. The residue is then dissolved in acetone and concentrated nitric acid is then dropped into the solution until pH 4.5 is obtained. 32 g of ethyl imidazo (2,1-b) thiazole-6-acetate nitrate cristallises; m.p. 102°–106° (acetone).

EXAMPLE 4

A solution of 4.25 g of ethyl-imidazo-(2,1-b)thiazole-6-acetate base (obtained from the nitrate salt prepared as described in Example 3) and 8 g of barium hydroxide octahydrate in 200 ml of water is refluxed for 2 hours. Sulfuric acid is then dropped into the solution until total precipitation of barium sulphate is obtained and no excess of $SO_4$ ions is present.

After filtering the precipitate off, the solution is washed with chloroform, and concentrated to ¼ of the initial volume to yield 3.2 g of imidazo-(2,1-b)thiazole-6-acetic acid; m.p. 193°–195°.

EXAMPLE 5

A solution of 15 g of 2-aminothiazole and 40.65 g of ethyl-α-bromo benzoyl acetate in 120 ml of absolute ethanol is refluxed for 12 hours. The solvent is evaporated and the residue is recristallised from isopropanol to yield 9 g of 5-carboethoxy-6-phenyl imidazo(2,1-b) thiazole hydrobromide; m.p. 198°–200°. The mother liquor is evaporated and the residue is dissolved in chloroform. After washing with alkaline water and drying, the solvent is evaporated and the residue is dissolved in ether. A solution of dry HCl in isopropanol is added until the pH is 3 to yield 10.2 g of 5-carboethoxy-6-phenyl-imidazo-(2,1-b) thiazole hydrochloride; m.p. 175°–178° (abs.ethanol).

EXAMPLE 6

18.6 g of 2-mercapto-4(5)-carboethoxy-5(4)-methyl imidazole(obtained by nitrosation of ethyl acetoacetate, reduction of the oxymino derivative to ethyl-α-amino acetoacetate and cyclisation with potassium thiocyanate) are stirred at room temperature in a solution of 2.3 g of sodium in 150 ml of abs. ethanol. 19.7 g of -bromoacetaldehyde diethyl acetal are added to the solution and the suspension obtained is refluxed for 12 hours. After cooling the precipitated sodium bromide is filtered off and the filtrate is evaporated. 28.7 g of 2-[4(5)-carboethoxy-5(4)-methylimidazolyl]-thioacetaldehyde diethyl acetal are obtained as an oil. The oil is dissolved in 150 ml of a 15% solution of hydrochloric acid and the solution is then stirred for 1 hour at room temperature. After neutralization with sodium bicarbonate 3-hydroxy-5-methyl-6-carbethoxy-imidazo-(2,1-b)2,3-dihydrothiazole, precipitates and is filtered off; m.p. 123°–124° (ethyl acetate).

13 g of the above compound are refluxed in 130 ml of phosphorus oxychloride; after vacuum evaporation of the solvent the residue is dissolved in ice-water, neutralized with sodium carbonate to yield, after filtration, 7 g of 5-methyl-6-carboethoxy-imidazo- (2,1-b)thiazole; m.p. 102°–103° (hexane).

EXAMPLE 7 a. The same reaction as described by Ochiai[-Ber.69,1650 (1936)] is performed, i.e., 2-mercapto-4(5)-carboethoxy-5(4)-methyl imidazole is reacted with chloroacetone at room temperature, to yield 2-thioacetonyl-4(5)-carboethoxy-5(4)-methylimidazole. Said imidazole derivative is reacted with phosphorus oxychloride to yield 3,5-dimethyl-6-carboethoxy-imidazo-(2,1-b) thiazole; m.p. 141°–142°.

b. A solution of 11.4 g of 2-amino-4-methyl thiazole and 21 g of ethyl α-bromo ethylglyoxalate in 200 ml of acetonitrile is refluxed for 5 hours in a nitrogen atmosphere and is then allowed to stand for one night at room temperature. After decolorization and evaporation of the solvent, the residue is dissolved in water and the solution obtained is neutralized with sodium carbonate. 16 g of 3,5-dimethyl-6-carboethoxy-imidazo-(2,1-b)thiazole precipitate and are filtered off; m.p. 141°–142° (ethyl acetate).

EXAMPLE 8 a. A solution of 15.8 g of 2-mercapto-4(5)-carbomethoxyimidazole and 10.17 g of chloracetone in 80 ml of abs.ethanol is refluxed for 20 hours. The solution is then cooled and ether is added to yield, after filtration, 16 g of 3-methyl-6-carbomethoxy-imidazo-(2,1-b)thiazole; m.p. 169°–174° (acetic acid).

b. A solution of 15.8 g of 2-mercapto-4(5)-carbomethoxyimidazole and 10.17 g of chloroacetone in 100 ml of abs.ethanol is refluxed for 2½ hours in a nitrogen atmosphere. The solution is concentrated and then ether is added to yield 25 g of 4(5)-carbomethoxy-2-acetonylthio imidazole hydrochloride. The base, having a m.p. 106.5°–107.5°, obtained from the hydrochloride is refluxed in 125 ml of $POCl_3$ for 2 hours. The solution is then concentrated under vacuum and ice-water is added to the residue. After neutralization with sodium bicarbonate the aqueous solution is extracted with chloroform. The solvent is then evaporated to yield 17 g of 3-methyl-6-carbomethoxyimidazo-(2,1-b)thiazole; m.p. 170°–173° (isopropanol).

EXAMPLE 9

5 g of 3-methyl-6-carbomethoxy-imidazo-(2,1-b)thiazole obtained as described in Example 8, are dissolved with stirring at room temperature in 100 ml of acetonitrile containing 10 ml of methyl iodide. After 24 hours 3 g of 3-methyl-6-carbomethoxy-imidazo-(2,1-b)thiazolium methyl iodide crystallise and are filtered off.

The filtrate is then evaporated and the residue is dissolved in water and the aqueous solution obtained is extracted with chloroform. The water is distilled off under vacuum and the residue obtained is continuously extracted with chloroform. After concentration ether is added to yield additional 2.5 g of the above quaternary salt, m.p. 179°–182° (dec.).

EXAMPLE 10

100 g of 3-methyl-6-carbomethoxy-imidazo-(2,1-b)thiazole (obtained as described in Example 8) are refluxed for 2 hours in 500 ml of an aqueous solution of 10% NaOH. Acetic acid is then dropped into the solution until the pH is 5. The solution is then cooled to yield, after filtration, 71 g of 3-methyl-imidazo-(2,1-b)thiazole-6-carboxylic acid; m.p. 245°–247°.

EXAMPLE 11

1 g of 3-methyl-imidazo-(2,1-b)thiazole-6-carboxylic acid obtained as described in Example 10 are refluxed in 10 ml of ethanol and a solution of 0.57 g of 2 amino-2-(hydroxymethyl)-1,3 propanediol in 10 ml of ethanol is added. After cooling is 1.5 g of 2'-(hydroxymethyl)-

1',3'-propanediol-2'-ammonium 3-methyl imidazo(2,1-b)thiazole 6-carboxylate precipitated, which were filtered off; m.p. 196°–197°.

EXAMPLE 12

1 g of 3-methyl-imidazo-(2,1-b)thiazole-6-carboxylic acid obtained as described in Example 10 are refluxed in 10 ml of ethanol and a solution of 0.49 g of 2-amino-2-methyl-1-propanol in 5 ml of ethanol is added. After cooling 1 g of 2'-methyl 1'-propanol 2'-ammonium 3-methylimidazo-(2,1-b)thiazole-6-carboxylate precipitated and were filtered off; m.p. 235°–238°.

EXAMPLE 13

1 g of 3-methyl-imidazo-(2,1-b)thiazole-6-carboxylic acid obtained as described in Example 10 are refluxed in 25 ml of ethanol and a solution of 0.55 g of triethylamine in 5 ml of ethanol is added. Ether is added to the cooled slution until an oily layer appears. The solvent is then evaporated to yield 1.4 g of oily triethylammonium-3-methyl-imidazo-(2,1-b)thiazole-6-carboxylate.

EXAMPLE 14

1 g of 3-methyl-imidazo-(2,1-b)thiazole-6-carboxylic acid obtained as described in Example 10 are refluxed in 25 ml of ethanol and a solution of 0.56 g of dimethylaminopropylamine in 2 ml of ethanol is added. The solvent is then evaporated to yield 1.5 g of oily, water-soluble 3'-dimethylaminopropyl-1'-ammonium 3-methyl-imidazo-(2,1-b)thiazole-6-carboxylate.

EXAMPLE 15

0.41 g of glycine methyl ester chlorhydrate are dissolved in 5 ml of water. The solution obtained is neutralized with sodium bicarbonate to pH 7 and then extracted quickly with 2 times 10 ml of chloroform. A boiling solution of 1 g of 3-methyl-imidazo-(2,1-b)thiazole-6-carboxylic acid obtained as described in Example 10 in 25 ml of ethanol is added to the above extract. After drying on sodium sulfate the solvent is evaporated to yield 1.2 g of oily, water-soluble methyl-ammoniumethanoate-3-methyl-imidazo-(2,1-b)thiazole-6-carboxylate.

EXAMPLE 16

To a solution of 6.3 g of phosphorus pentachloride in 120 ml of dry methylene chloride, 5 g of 3-methyl-imidazo-(2,1-b)thiazole-6-carboxylic acid(prepared as described in Example 10) is added and the suspension obtained is refluxed for 3 hours. After vacuum evaporation of the solvent the residue obtained being 3-methyl-imidazo-(2,1-b)thiazole-6-carboxylchloride chlorohydrate is dissolved in 100 ml of abs.ethanol and the solution is refluxed for 4 hours. The solvent is removed and the residue obtained is dissolved in water. The solution obtained is neutralised to pH 7.5 to yield 5 g of 3-methyl-6-carboethoxyimidazo-(2,1-b)thiazole; m.p. 117°–119°.

EXAMPLE 17

In a manner analogous to that described in Example 16 4.8 g of 3-methyl-6-carbopropoxy-imidazo-(2,1-b)thiazole are prepared; m.p. 79°–81°.

EXAMPLE 18

In a manner analogous to that described in Example 16 3.5. g of 3-methyl-6-carboisopropoxy-imidazo-(2,1-b)thiazole are prepared; m.p. 96°–98° (the reaction time between the acyl chloride and the alcohol is about 24 hours).

EXAMPLE 19

In a manner analogous to that described in Example 16 4.8 g of 3-methyl-6-carbobutoxy-imidazo-(2,1-b)thiazole are prepared; m.p. 79°–83°.

EXAMPLE 20

In a manner analogous to that described in Example 16 4.2 g of 3-methyl-6-carboisobutoxy-imidazo-(2,1-b)thiazole are prepared; m.p. 80.5°–81.5° (hexane).

EXAMPLE 21

In a manner analogous to that described in Example 16 4.5 g of 3-methyl-6-sec.carbobutoxy-imidazo-(2,1-b)thiazole are prepared; m.p. 84°–86° (hexane). (The reaction time between the 3-methyl-imidazo-(2,1-b)thiazole-6-carboxyl chloride and the sec.butanol is about 14 hours).

EXAMPLE 22

In a manner analogous to that described in Example 16 5.5 g of 3-methyl-6-carbooctanoxy-imidazo-(2,1-b)thiazole are prepared; m.p. 72°–75° (hexane/petroleum ether).

EXAMPLE 23

In a manner analogous to that described in Example 13 4.5 g of 3-methyl-6-carbocyclohexanoxy-imidazo-(2,1-b)thiazole are prepared; m.p. 127°–129° (hexane/chloroform).

EXAMPLE 24

100 ml of dry ethyl amine is dropped into the acyl chloride obtained as described in Example 16 and the temperature is kept at $-20°$. The solution obtained is stirred for 1 hour at 0° and for 1 hour at 10°. The solvent is then evaporated and the residue is neutralized with an aqueous sodium carbonate solution and then extracted with chloroform. The solvent is then removed and an oil is obtained. Said oily residue is dissolved in ethyl acetate and conc.nitric acid is added by way of dropping until the pH is 3.6 g of 3-methyl-6-ethylcarboxamide-imidazo-(2,1-b)thiazole nitrate are obtained; m.p. 135°–139° (methyl-ethyl-ketone),(dec.)

EXAMPLE 25

In a manner analogous to that described in Example 24 6 g of 3-methyl-6-diethylcarboxamide-imidazole-(2,1-b)thiazole nitrate are prepared; m.p. 130°–132° (dec.) (The reaction is performed at the boiling temperature of diethylamine).

EXAMPLE 26 a. 48 g of 3-methyl-6-carbomethoxy-imidazo-(2,1-b)thiazole, prepared as described in Example 8, suspended in 400 ml of dry tetrahydrofuran (THF) is dropped into a suspension of 12 g of LiAlH$_4$ in 150 ml of dry THF. The reaction temperature is kept at 25°–30°. After the reaction has terminated, the suspension is kept for 1 hour at room temperature and the excess LiAlH$_4$ is destroyed by adding ethyl acetate and water.

The suspension is filtered and the cake obtained is washed with hot ethanol and the combined solutions are concentrated to yield 34 g of 3-methyl-6-hydroxymethyl-imidazo-(2,1-b)thiazole; m.p. 156°–157° (methyl-ethyl-ketone).

b. 100 ml of a 70% solution of NaAlH$_2$(CH$_3$OCH$_2$CH$_2$O)$_2$ in benzene are dropped at 25° into a suspension of 25 g of 3-methyl-6-carbomethoxy-imidazo-(2,1-b)thiazole, prepared as described in Example 8, in 250 ml of dry THF. The suspension is stirred for 2 hours at room temperature and thereafter 25 ml of water are slowly added. The suspension is then filtered and the filtrate concentrated to yield 21 g of 3-methyl-6-hydroxymethyl-imidazo-(2,1-b)thiazole; m.p. 155°–156° (methyl-ethyl-ketone).

EXAMPLE 27

10 g of 3-methyl-6-hydroxymethyl-imidazo-(2,1-b)thiazole prepared as described in one of the methods in Example 26, is refluxed for 2 hours in 100 ml of SOCl$_2$. The solution is then cooled, 50 ml of ether are added to yield 11 g of 3-methyl-6-chloromethyl-imidazo-(2,1-b)thiazole hydrochloride; m.p. 280°.

EXAMPLE 28

3.4. g of 3-methyl-6-chloromethyl-imidazo-(2,1-b)thiazole hydrochloride, prepared as described in Example 27, is introduced with stirring into a cooled solution of 3.5 g of sodium phenate in 100 ml of THF. After about 1 hour the sodium chloride which precipitates is filtered off, the solvent is evaporated and acidic water is added to the residue. The aqueous solution is extracted, at pH 3–6, with chloroform. The pH is then raised to 7–7.5 and the aqueous solution is again extracted with chloroform. This extract is dried and the solvent is then evaporated to yield 4 g of 3-methyl-6-phenoxymethylimidazo-(2,1-b)thiazole; m.p. 190°–192° (methyl-ethyl-ketone).

EXAMPLE 29

3.4 g of 3-methyl-6-chloromethyl-imidazo-(2,1-b)thiazole are slowly added into 50 ml of cooled and stirred morpholine. The stirring is continued for 1 hour at room temperature and another hour at 40°–50°. The suspension obtained is filtered and the filtrate is evaporated. The residue obtained is dissolved in water and the aqueous solution obtained is extracted with chloroform. The chloroform solution is washed at pH 5–6 with water and after drying it is evaporated. Ethyl acetate is added to the residue to yield 4.5 g of 3-methyl-6-morpholinomethyl-imidazo-(2,1-b)thiazole; m.p. 203°–204° (methyl-ethyl-ketone).

EXAMPLE 20

A solution of 5 g of 3-methyl-6-hydroxymethyl-imidazo-(2,1-b)thiazole in 100 ml of dry chloroform is dropped at 35° into a solution of 15 ml of butyroyl chloride and 12 ml of pyridine in 75 ml of dry chloroform. The suspension obtained is stirred for 1 hour at room temperature and then filtered. The filtrate is concentrated by evaporation. The residue obtained is dissolved in abs.ethanol and a stream of dry hydrochloric acid is bubbled into the solution to yield 4.5 g of 3-methyl-6-butyroxymethyl-imidazo-(2,1-b)thiazole hydrochloride; m.p. 126°–128°.

EXAMPLE 31

A solution of 5 g of 5-methyl-6-hydroxymethyl-imidazo-(2,1-b)thiazole in 100 ml of dry chloroform is dropped at room temperature into a solution of 20 ml of p-chlorobenzoyl chlorine and 12 ml of pyridine in 75 ml of dry chloroform. The solution is stirred for 30 minutes at room temperature and filtered. The filtrate is concentrated under vacuum; the residue obtained is dissolved in isopropanol and a stream of dry hydrogen chloride is bubbled into the solution to yield 6 g of 3-methyl-6-p-chlorobenzoyloxymethyl-imidazo-(2,1-b)thiazole hydrochloride; m.p. 198°–199°.

EXAMPLE 32

15.8 g of 2-mercapto-4(5)-carbomethoxy-imidazole are suspended in a solution of 15.8 g of bromomethyl-ethyl-ketone (prepared by brominating methyl-ethyl-ketone in the presence of an equivalent of potassium chlorate in water; m.p. 75°–80°/60 mm Hg; 103°–105°/150 mm Hg) in 100 ml of abs.ethanol. The suspension obtained is stirred for 1 hour and then allowed to stand over night at room temperature. The solvent is then evaporated. The residue is dissolved in water, then neutralized with an aqueous 5% sodium carbonate solution until pH 6.5 is obtained. The solution is extracted with chloroform and the chloroform is then evaporated in order to yield 23 g of the semicrystalline 4(5)-carbomethoxy-2-(γ-methylacetonylthio)-imidazole. Said compound is refluxed for 5 hours in 230 ml of phosphorus oxychloride. The solvent is then evaporated; ice-water is added to the residue and the solution is neutralised with sodium carbonate to yield 16 g of 3-ethyl-6-carbomethoxy-imidazo-(2,1-b)thiazole; m.p. 147°–149° (ethyl acetate).

EXAMPLE 33

15.8 g of 2-mercapto-4(5)-carbomethoxy-imidazole are suspended in a solution of 16.5 g of bromomethyl-propyl-ketone (prepared by brominating methyl-propyl-ketone in the presence of an equivalent of potassium chlorate in water; b.p. 88°–94°/50 mm Hg) in 100 ml of abs.ethanol. The suspension is then stirred for 2 hours at room temperature and the solution obtained is allowed to stand over night. The solvent is then evaporated. The residue obtained is dissolved in water, then neutralized with an aqueous 5% sodium carbonate solution. The solution is then extracted with chloroform and the chloroform is evaporated to yield 24 g of oily 4(5)-carbomethoxy-2-(γ-ethylacetonylthio)-imidazole.

Said oil is refluxed for 3 hours in 250 ml of phosphorus oxychloride. The solvent is evaporated under vacuum; icewater is added and the solution obtained is neutralized with sodium carbonate and extracted with chloroform. The solvent is evaporated to yield 14 g of 3-propyl-5-carbomethoxy-imidazo-(2,1-b)thiazole; m.p. 149°–150° (abs.ethanol).

EXAMPLE 34

15.8 g of 2-mercapto-4-(5)-carbomethoxy-imidazole are suspended in a solution of 18 g of α-bromomethyl-t.-butyl-ketone(prepared by brominating pinacoline in the presence of catalytic amounts of anhydrous aluminium chloride; b.p. 88.5°–90°/17 mm Hg) in 100 ml of abs.ethanol. The suspension obtained is stirred for ½ hour at room temperature and then allowed to stand over night. The bromohydrate of 4(5)-carbomethoxy-2-γ,γ,γ,-trimethyl-acetonylthio)-imidazole precipitates and is filtered off. After neutralization of the salt 19 g of the free base is obtained; m.p. 110°–111° (ether).

The above base is refluxed for 12 hours in 190 ml of phosphorus oxychloride. (the cyclisation reaction is not complete and some starting product can be found at the end of the reaction). The solvent is evaporated under vacuum; the residue is dissolved in ice-water and the solution obtained is neutralized with sodium carbonate and then extracted with chloroform. The residue obtained after the evaporation of the solvent is chromatographed on neutral aluminium oxide and eluted with a chloroform/petroleum-ether 40°-60° mixture (20/80) to yield 5.4 g of 3-t.butyl-6-carbomethoxy-imidazo-(2,1-b)-thiazole; m.p. 134°-135°.

EXAMPLE 35

A solution of 15.8 g of 2-mercapto-4(5)-carbomethoxyimidazole and 22 g of ω-bromo acetophenone [prepared as described in Zhuk.Obshch.Khim 33, 1135 (1963)] in 100 ml of abs.ethanol is stirred for 2½ hours at room temperature. 30 g of 4(5)-carbomethoxy-2-phenacylthio-imidazole hydrobromide are filtered off.

The free base, crystallized from acetone, is refluxed for 5 hours in 250 ml of phosphorus oxychloride. The solvent is evaporated under vacuum. The residue obtained is dissolved in ice-water, the solution is neutralized with sodium bicarbonate until pH 6 is obtained and then extracted with chloroform. The extract is dried and the solvent is evaporated to yield 21 g of 3-phenyl-6-carbomethoxy-imidazo-2,1-b)thiazole; m.p. 172°-173° (acetone).

EXAMPLE 36

A solution of 15.8 g of 2-mercapto-4(5)-carbomethoxy-imidazole and 25 g of ω-bromo-p-chloroacetophenone (prepared by brominating 17 g of p-chloroacetophenone in dioxane/ether 1:2) in 150 ml of abs.ethanol is stirred for 2 hours at room temperature. 200 ml of ether are then added to yield 34 g of the hydrobromide of 4(5)-carbomethoxy-2-(p-chlorophenacylthio)-imidazole.

30 g of the free base obtained from said hydrobromide is refluxed for 10 hours in 250 ml of phosphurus oxychloride. The solvent is then evaporated under vacuum; ice and chloroform are added to the residue and sodium carbonate is slowly added to the solution until pH 7. The chloroform layer is separated, dried and evaporated to yield 17 g of 3-p-chlorophenyl-6-carbomethoxy-imidazo-(2,1-b)thiazole; m.p. 229°-230° (dec.)(methanol).

EXAMPLE 37

A solution of 15.8 g of 2-mercapto-4(5)-carbomethoxy-imidazole and 29.7 g of ω-bromo-p-phenylacetophenone (prepared by brominating 21 g of p-phenylacetophenone in dioxane/ether 1:2) in 400 ml of abs. ethanol and 250 ml of dry methylene chloride is stirred for 2 hours at room temperature. 37 g of the hydrobromide of 4(5)-carbomethoxy-2-(p-phenylphenacylthio)-imidazole is obtained.

29 g of the free base obtained from said hydrobromide is refluxed for 7 hours in 300 ml of phosphurus oxychloride. The solution is then worked up in the manner described in Example 36 to yield 22 g of 3-p-phenyl-phenyl-6-carbomethoxy-imidazo-(2,1-b)thiazole; m.p. 186°-188° (acetonitrile).

EXAMPLE 38

A solution of 15.8 g of 2-mercapto-4(5)-carbomethoxy-imidazole and 25 g of ω-bromo-β-acetonaphtone[prepared according to J.O.C. 11, 21 (1946)] in 150 ml of abs.ethanol is stirred for 2 hours at room temperature. 25 g of the hydrobromide of 4(5)-carbomethoxy-2-naphthacylthio-imidazole is obtained. Said salt is neutralized to yield 21 g of the free base; m.p. 162°-163.5° (abs.ethanol).

The base is refluxed at least 36 hours in 200 ml of phosphorous oxychloride and the solution is then worked up in a manner similar to that described in Example 36 to yield 12 g of 3-(β-naphthyl)-6-carbomethoxy-imidazo-(2,1-b)thiazole; m.p. 187°-188°.

EXAMPLE 39

15.8 g of 2-mercapto-4(5)-carbomethoxy imidazole are suspended in a solution of 19 g of ω-bromomethyl-α-furyl-ketone (prepared by brominating methyl-α-furyl-ketone in dioxane/ether) in 150 ml of abs.ethanol and the suspension is then stirred for 2 hours at room temperature to yield 26 g of hydrobromide of 4(5)-carbomethoxy-2-(α-furacylthio)-imidazole. After neutralization 20 g of the free base are obtained; m.p. 139°-141° (ethyl acetate).

The base is refluxed for 12 hours in 200 ml of phosphorus oxychloride. The solvent is then evaporated under vacuum, the residue is dissolved in water and 3-(2'-furyl)-6-carbomethoxy-imidazo(2,1-b)thiazole hydrochloride is filtered off. After neutralization the free base is obtained; m.p. 169°-170° (methyl-ethyl-ketone).

EXAMPLE 40

15.8 g of 2-mercapto-4(5)-carbomethoxy-imidazole are suspended in a solution of 20.5 g of ω-bromomethyl-α-thienyl-ketone (prepared by brominating methyl-α-thienyl-ketone in dioxane/ether) in 150 ml of abs.ethanol. The suspension is then stirred for 2 hours and thereafter allowed to stand over night at room temperature to yield 26 g of the hydrobromide of 4(5)-carbomethoxy-2-(α-thienacylthio)-imidazole.

Said salt is dissolved in water, the solution is neutralised with sodium carbonate and extracted with chloroform. The extract is evaporated to yield 22 g of the free base; m.p. 125°-126° (ethyl acetate).

The base is refluxed for 10 hours in 200 ml of phosphorus oxychloride. The solvent is then evaporated under vacuum. The residue is dissolved in ice-water, the solution obtained is neutralised with sodium carbonate and extracted with chloroform. The solvent is evaporated to yield 17.5 g of 3-(2'-thienyl)-6-carbomethoxy-imidazo-(2,1-b)thiazole; m.p. 161.5°-163.0° (abs.ethanol).

EXAMPLE 41

15.8 g of 2-mercapto-4(5)-carbomethoxy-imidazole and 21.45 g of ethyl bromopyruvate are dissolved in 200 ml of abs.ethanol and the solution is stirred for 2 hours at room temperature. The solvent is evaporated, water and chloroform are added to the residue and the solution obtained is neutralized with sodium carbonate. After extraction with chloroform, drying, decolorization and evaporation of the solvent 36 g of ethyl-α-oxo-[4(5)-carbomethoxy-2-imidazolyl]-thiopropionate are obtained.

Said compound is refluxed for 2 hours in 360 ml of phosphorus oxychloride. The solvent is evaporated and water and chloroform are added to the residue. The solution is neutralized with sodium carbonate and then extracted with chloroform. The chloroform is then evaporated to yield 18.5 g of 3-carboethoxy-6-carbomethoxy-imidazo-(2,1-b)thiazole; m.p. 187°-189° (ethyl acetate).

EXAMPLE 42

A solution of 15.8 g of 2-mercapto-4(5)-carbomethoxy-imidazole and 20.9 g of ethyl-bromo acetoacetate in 250 ml of acetonitrile is stirred for 24 hours at room temperature. After decolorization the solvent is evaporated and the residue is dissolved in a mixture of chloroform and water; sodium carbonate is then added until pH 7.5 is reached. The water phase is extracted several times with chloroform and the chloroform phase sometimes with water. The chloroform extracts are combined, dried and the solvent is then evaporated to yield 32.5 g of oily ethyl-2-[4(5)-carbomethoxy-2-imidazolyl]-thioacetoacetate.

The oil is refluxed for 15 minutes in 180 ml of phosphorus oxychloride. The solvent is evaporated, under vacuum, the residue is dissolved in water and the solution obtained is neutralized with sodium bicarbonate and extracted with chloroform. The chloroform extract is dried, the solvent is evaporated and the residue obtained is dissolved in a benzene-ether mixture. The solution is concentrated to yield 14 g of ethyl-6-carbomethoxy-imidazo-(2,1b)thiazole-3-acetate; m.p. 152°–154°.

EXAMPLE 43

A solution of 15.8 g of 2-mercapto-4(5)-carbomethoxy-imidazole and 16.6 g of α-bromovaleraldehyde (prepared by direct bromination of n-valeraldehyde; b.p. 36°–38°/4 mmHHg) in 100 ml of abs.ethanol is stirred for 24 hours at room temperature. 4.5 g of the unreacted imidazole are filtered off, the solvent is evaporated and the residue dissolved in a water-chloroform mixture. The solution is neutralized with sodium carbonate and extracted with chloroform. The chloroform is evaporated to yield 11 g of 4(5)-carbomethoxy-2-(-formylbutylthio)-imidazole; m.p. 160°–162°.

Said compound is refluxed for 4 hours in 110 ml of phosphorus oxychloride. The solvent is evaporated. The residue obtained is dissolved in ice-water and the solution is neutralized with sodium carbonate to yield 10.5 g of 2-propyl-6-carbomethoxy-imidazo-(2,1-b)thiazole; m.p. 155°–156° (methyl-ethyl-ketone).

EXAMPLE 44

A solution of 15.8 g of mercapto-4(5)-carbomethoxy-imidazole and 15.1 g of α-bromoethyl-methyl-ketone(-prepared in an analogous manner to that described in Example 32; b.p. 87°–88°/150 mm Hg) in 120 ml of abs.ethanol is stirred for 2 hours at room temperature and then allowed to stand over night. The solution is then evaporated, the residue obtained is dissolved in water and the solution is neutralised with sodium carbonate and extracted with chloroform. The chloroform is evaporated to yield 23 g of semicrystalline 4-(5)-carbomethoxy-2-(α-methyl-acetonylthio)-imidazole.

Said compound is refluxed for 3 hours in 230 ml of phosphorus oxychloride. The solvent is evaporated, the residue is dissolved in ice-water and the solution is neutralized with sodium carbonate to yield 17 g of 2,3-dimethyl-6-carbomethoxy-imidazo(2,1-b)thiazole; m.p. 180°–181° (abs.ethanol).

EXAMPLE 45

A suspension of 15.8 g of 2-mercapto-4(5)-carbomethoxy-imidazole in a solution of 16.5 g of α-bromopropyl-methyl-ketone(prepared in analogous manner to that described in Example 33; b.p. 76°–82°/50 mm Hg) in 100 ml of abs.ethanol is stirred for 2 hours at room temperature and allowed to stand over night. The solution obtained is evaporated and the residue is dissolved in water. The solution is neutralized with sodium carbonate and extracted with chloroform. The extract is evaporated to yield 22 g of 4(5)-carbomethoxy-2-(α-ethyl-acetonylthio)-imidazole; m.p. 105°–106°.

Said compound is refluxed for 2½ hours in 200 ml of phosphorus oxychloride. The solution is evaporated, the residue is dissolved in ice-water, the solution obtained is neutralized with sodium carbonate and extracted with chloroform. The solvent is evaporated to yield an oil which upon washing with ether yields 14 g of 2-ethyl-3-methyl-6-carbomethoxy-imidazo-(2,1-b)thiazole; m.p. 94°–95°.

In a similar manner the following compounds were prepared:
2-propyl-3-methyl-6-carboethoxy-imidazo-(2,1-b)thiazole
2-butyl-3-methyl-6-carboethoxy-imidazo-(2,1-b)thiazole
2-isoamyl-3-methyl-6-carboethoxy-imidazo-(2,1-b)thiazole

EXAMPLE 46

A solution of 15.8 g of 2-mercapto-4(5)-carbomethoxyimidazole and 23.4 g of α-bromobenzyl-methyl-ketone in 150 ml of abs. ethanol is stirred for 1 hour at room temperature. The solvent is distilled off and the residue is dissolved in water. The solution is neutralized with sodium carbonate and extracted with chloroform. The extract is dried and the chloroform is evaporated to yield 38.5 g of an oil being 4(5)-carbomethoxy-2-(α-phenyl-acetonylthio)-imidazole.

The oil is refluxed for 1 hour in 200 ml of phosphorus oxychloride and the solvent is then evaporated under vacuum. The residue is dissolved in ice-water and sodium bicarbonate is added to the solution obtained until pH 7.5. The solution is extracted with chloroform. The extract is dried and evaporated to yield 17 g of 2-phenyl-3-methyl-6-carbomethoxy-imidazo-(2,1-b)thiazole; m.p. 155°–157° (ethyl acetate).

EXAMPLE 47

A solution of 15.8 g of 2-mercapto-4(5)-carbomethoxy-imidazole and 17.7 g of α-bromo cyclohexanone in 150 ml of dry butanol are heated at 80° for 1 hour. The solvent is then distilled off under vacuum and the residue obtained is dissolved in water. The solution obtained is neutralized with sodium carbonate and extracted with chloroform. The extract is dried, the solvent is evaporated and the residue is chromatographed on an alumina column to yield 14.5 g of 2-carbomethoxy-imidazo-(2,1-b)-5,6,7,8-tetrahydro-benzothiazole; m.p. 97°–99°(petroleum-ether/ether mixture).

EXAMPLE 48

0.5 g of NaBH$_4$ are slowly introduced in a stirred solution of 5.5 g of 4(5)-carbomethoxy-2-acetonylthio-imidazole (prepared as described in Example 8b) in 60 ml of methanol. The temperature is kept at 5°–10°. The solution is stirred for 1 hour at said temperature and then the solvent is evaporated. Water is added to the residue and the solution is neutralised with sodium carbonate to yield 5.2 g of 4(5)-carbomethoxy-2-(β-hydroxy-propylthio)-imidazole; m.p. 153°–154°.

Said compound is refluxed for 2 hours in 55 ml of phosphorus oxychloride and the residue obtained after the evaporation of the solvent is dissolved in ice-water.

The solution obtained is neutralized with sodium carbonate and extracted with chloroform. The extract is evaporated and 3.2 g of 3-methyl-6-carbomethoxy-imidazo-(2,1-b)-2,3-dihydrothiazole are obtained; m.p. 94°-95°(ether).

EXAMPLE 49

4.5 g of 2,3-dimethyl-6-carbomethoxy-imidazo-(2,1-b)thiazole(prepared as described in Example 44) are refluxed for 2 hours in 25 ml of 10% NaOH. The solution obtained is cooled to 40° and acetic acid is dropped into the solution until the pH is 5. The solution is then cooled to yield after filtration 4.1 g of 2,3-dimethyl-imidazo-(2,1-b)thiazole-6-carboxylic acid; m.p. 260°-261°.

EXAMPLE 50

1.5 g of 2-ethyl-3-methyl-6-carbomethoxy-imidazo-(2,1-b)thiazole(obtained as described in Example 45) are refluxed for 2 hours in 5 ml of 10% NaOH. The solution obtained is treated in the same manner as described in Example 49 to yield 1.2 g of 2-ethyl-3-methyl-imidazo-(2,1-b)thiazole-6-carboxylic acid m.p. 243°-245° C.

EXAMPLE 51

2.1 g of 2-ethyl-3-methyl-imidazo-(2,1-b)thiazole-6-carboxylic acid obtained as described in Example 50, are refluxed in 50 ml of ethanol and a solution of 1.2 g of 2-amino-2-(hydroxymethyl)-1,3-propanediol in 10 ml of ethanol is added. The solvent is then evaporated to yield 3 g of 2'-(hydroxymethyl)-1',3'-propanediol-2'-ammonium-2-ethyl-3-methyl-imidazo-(2,1-b)thiazole-6-carboxylate; m.p. 164°-165°(isopropanol).

EXAMPLE 52

1 g of 2-ethyl-3-dimethyl-imidazo-(2,1-b)thiazole-6-carboxylic acid obtained as described in Example 50 are refluxed in 20 ml of ethanol and a solution of 0.75 g of triethanolamine in 5 ml of ethanol is added to the solution. The solvent is then evaporated and an oily salt being triethanolammonium-2-ethyl-3-methyl-imidazo-(2,1-b)thiazole-6-carboxylate is obtained.

EXAMPLE 53

2.5 g of 2,3-dimethyl-imidazo-(2,1-b)thiazole-6-carboxylic acid (prepared as described in Example 49) are added to a solution of 3.3 g of phosphorus pentachloride in 70 ml of dry methylene chloride and the suspension obtained is refluxed for 3 hours. After vacuum evaporation of the solvent, the residue is dissolved in 100 ml of abs. ethanol and the solution is then refluxed for 24 hours. The solvent is then evaporated and the residue is dissolved in water and the solution is neutralized with $Na_2CO_3$. After extraction with chloroform and evaporation to dryness, 2.1 g of 2,3-dimethyl-6-carbethoxy-imidazo-(2,1-b)thiazole are obtained; m.p. 108°-110° C.(acetone).

EXAMPLE 54

In a manner analogus to that described in Example 53, there are prepared from 5 g of 2-ethyl-3-methyl-imidazo-(2,1-b)-thiazole-6 carboxylic acid (prepared as described in Example 51) 4.8 g of 2-ethyl-3-methyl-6-carboethoxy-imidazo-(2,1-b)thiazole; m.p. 64°-65°(ether/petrol ether).

EXAMPLE 55

100.000 Tablets are prepared utilising the following substances:

| A. | 3-Methyl-imidazo-(2,1-b)thiazole-6-carboxylic acid | 25 kg |
|---|---|---|
|  | Amylum B.P. | 3 kg |
|  | Lactose B.P. | 15 kg |
| B. | Granulate with 10% mucilage Amylum | |
| C. | Amylum B.P. | 2 kg |
| D. | Amylum B.P | 2 kg |
|  | Talc B.P | 2 kg |
|  | Magnesium Stearate | 1 kg |

The tablets are prepared as follows:

Substances A and B are granulated together. Thereafter compound C is added which yields a wet granulate mix. This mix is dried and then crushed. Compounds D are then admixed with the previous mix and tablets are prepared from the final mix.

EXAMPLE 56

100.000 Long-acting tablets are prepared utilizing the following substances:

| A. | 2-Ethyl-3-methyl-6-carboethoxy-imidazo-(2,1-b)thiazole | 25 | kg |
|---|---|---|---|
| B. | Oleum Theobrom | 1 | kg |
|  | Carnauba wax Pale | 1.3 | kg |
|  | Cera Alba B.P. | 1.3 | kg |
|  | Stearic acid Triple Pressed | 0.6 | kg |
|  | Non emulsifying Glyceryl Monostearate | 1.6 | kg |
|  | Trichloroethylene | 3 | kg |
| C. | Magnesium Stearate | 0.6 | kg |
|  | Carborol | 3 | kg |

The tablets are prepared as follows:

Substances A and B are granulated together. The mixture obtained is dried and then crushed. The crushed mixture is admixed with substances C. Tablets are prepared from the mixture obtained.

EXAMPLE 57

Some of the new compounds according to the present invention were tested on diabetic alloxan treated rats (blood glucose concentration 250-450 mg/100 ml) -diabetic rats. In the test a 200 mg/kg dose was orally administered and a curve response dose was then performed.

The blood glucose concentration was determined at 0-5-24 hours after the oral administration. In some cases a curve time response was determined at 0-3-5-8-24 hours.

The influence of the products on hyperglicaemic glucose-loaded rats and on normal rats by oral or intraperitoreal administration was also determined for some compounds. The glucose concentration in the urine was also checked and in many cases the general pharmacological screening was carried out.

Some of the results are given in the following Tables I-V, where $\Delta$ mean is the mean diminution of the blood glucose concentration (mg/100 ml) in "n" experiments at the cited hour and $$\Delta\% \text{ mean} = \frac{\Delta\text{mean} \cdot 100}{\text{mean starting blood glucose concentration}}$$

All compounds are those of formula I and substituents A, B, C and D refer to those given in said formula.

TABLE I

Diabetic - alloxane treated rats

| A | B | C | D | n | dose P.O. mg/kg. | 5 hours Δ | 5 hours Δ% | 24 hours Δ | 24 hours Δ% |
|---|---|---|---|---|---|---|---|---|---|
| $C_6H_5$ | $COOC_2H_5$ | H | H | 10 | 200 | 46 | | 27 | |
| $COOC_2H_5$ | $CH_3$ | $CH_3$ | H | 10 | 200 | 57 | | 37 | |
| $COOCH_3$ | H | $CH_3$ | H | 62 | 200 | 104 | 24% | 23 | |
| $COOC_2H_5$ | H | $CH_3$ | H | 10 | 50 | 40 | | 10 | |
| | | | | 10 | 100 | 81 | | 18 | |
| | | | | 40 | 200 | 139 | 39% | 37 | |
| $COOC_2H_5 HCl$ | H | $CH_3$ | H | 15 | 200 | 165 | 48% | 13 | |
| $COOCH(CH_3)_2$ | H | $CH_3$ | H | 20 | 200 | 118 | | 36 | |
| $COOCH_2CH(CH_3)_2$ | H | $CH_3$ | H | 10 | 200 | 135 | 37% | 60 | 16% |
| $COOH \cdot HCl$ | H | $CH_3$ | H | 15 | 200 | 160 | 49% | 15 | |
| COOH | H | $CH_3$ | H | 40 | 200 | 118 | 35% | 44 | |
| (+) $COONH_3C(CH_2OH)_3$ | H | $CH_3$ | H | 15 | 60 | 47 | | 13 | |
| | | | | 15 | 120 | 90 | | 25 | |
| | | | | 15 | 180 | 115 | 32% | 33 | |
| $CH_2OH$ | H | $CH_3$ | H | 20 | 200 | 74 | | 0 | |
| $CH_2OCOC_3H_7$ | H | $CH_3$ | H | 10 | 200 | 73 | | 0 | |
| $CH_2OCOCl(p)$ | H | $CH_3$ | H | 15 | 200 | 100 | | 0 | |
| $COOCH_3$ | H | $C(CH_3)_3$ | H | 10 | 200 | 80 | | 31 | |
| $COOCH_3$ | H | $C_6H_5$ | H | 10 | 200 | 72 | | 10 | |
| $COOCH_3$ | H | H | $C_3H_7$ | 10 | 200 | 73 | | 7 | |
| $COOC_2H_5$ | H | $CH_3$ | $CH_3$ | 10 | 200 | 142 | 41% | 67 | 20% |
| (+) $COONH_3C(CH_2OH)_3$ | H | $CH_3$ | $C_2H_5$ | 15 | 30 | 30 | | 0 | |
| | | | | 15 | 60 | 70 | | 25 | |
| | | | | 15 | 120 | 104 | | 31 | |
| | | | | 15 | 180 | 150 | 46% | 50 | 15% |
| | | | | 15 | 360 | 150 | 44% | 104 | 29% |
| $COOC_2H_5$ | H | $CH_3$ | $C_2H_5$ | 10 | 50 | 47 | | — | |
| | | | | 10 | 100 | 73 | | — | |
| | | | | 50 | 200 | 144 | 45% | 80 | 25% |
| | | | | 15 | 400 | 176 | 52% | 97 | 28% |
| $COOC_2H_5 \cdot HCl$ | H | $CH_3$ | $C_2H_5$ | 15 | 200 | 146 | 46% | 29 | <10% |
| $COOC_2H_5$ | H | $CH_3$ | $CH_2CH_2CH(CH_3)_2$ | 10 | 200 | 154 | 47% | 87 | 27% |
| $COOCH_3$ | H | $CH_3$ | $C_6H_5$ | 10 | 200 | 83 | 21% | 64 | 16% |
| (+) $COONH(CH_2CH_2OH)_3$ | H | $CH_3$ | $C_2N_5$ | 10 | 200 | 170 | 50% | 0 | |
| Control phenformine | | | | 135 | 200 | 99 | 28% | | |

TABLE II

Diabetic-glucose loaded rats

| A | B | C | D | n | dose P.O. mg/kg | 5 hours Δ | 5 hours Δ% | 24 hours Δ | 24 hours Δ% |
|---|---|---|---|---|---|---|---|---|---|
| $COOC_2H_5 \cdot HCl$ | H | $CH_3$ | H | 10 | 100 | | 53% | 0 | |
| $COOC_2H_5 \cdot HCl$ | H | $CH_3$ | $C_2H_5$ | 10 | 100 | | 34% | | |
| (+) $COONH_3C(CH_2OH)_3$ | H | $CH_3C$ | $C_2H_5$ | 10 | 100 | | 55% | 0 | |

TABLE III

Normal rats

| A | B | C | D | n | dose P.O. mg/kg | 5 hours Δ | 5 hours Δ% | 24 hours Δ | 24 hours Δ% |
|---|---|---|---|---|---|---|---|---|---|
| $COOC_2H_5$ | H | $CH_3$ | H | 10 | 200 | 23 | | 11 | |
| COOH | H | $CH_3$ | H | 10 | 200 | 14.5 | | 5 | |
| $CH_2OCOCl(p)$ | H | $CH_3$ | H | 10 | 200 | 17 | | 14 | |
| $COOH \cdot HCl$ | H | $CH_3$ | H | 10 | 100IP | — | 21 | 0 | |
| $COOC_2H_5 \cdot HCl$ | H | $CH_3$ | $C_2H_5$ | 10 | 50 I.P. | — | 24% | 0 | |
| | | | | | 100 I.P. | — | >70% | | 5% |
| (+) $COONH_3C(CH_2OH)_3$ | H | $CH_3$ | $C_2H_5$ | 10 | 100 I.P. | — | 38% | | 15% |

TABLE IV

Influence of starting blood glucose concentration on Δ mean and Δ% means (5 hours after per os administration)

| A | B | C | D | dose P.O. | starting blood glucose concentration | | | | | |
|---|---|---|---|---|---|---|---|---|---|---|
| | | | | | <290 | | 290–380 | | >380 | |
| | | | | | Δ | Δ | Δ | Δ% | Δ | Δ% |
| COOCH₃ | H | CH₃ | H | 200 | 52 | 20 | 120 | 30 | 163 | 39 |
| COOC₂H₅ | H | CH₃ | H | 200 | 85 | 35 | 127 | 37 | 233 | 55 |
| COOH | H | CH₃ | H | 200 | 85 | 37 | 156 | 45 | 196 | 48 |
| CH₂OCOφCl(p) | H | CH₃ | H | 200 | 47 | 17 | 105 | 34 | 125 | 35 |
| COOC₂H₅ | H | CH₃ | C₂H₅ | 200 | 120 | 41 | 145 | 43 | 165 | 41 |
| control phenformine | | | | 200 | 135 | 44 | 95 | 26 | 50 | 8 |

TABLE V

Influence of time on Δ mean in diabetics alloxane-treated rats

| A | B | C | D | dose P.O. | |
|---|---|---|---|---|---|
| COOC₂H₅ | H | CH₃ | H | 200 | 5 hours Δ = 139 |
| | | | | | 8 hours Δ = 45 |
| | | | | | 24 hours Δ = 37 |
| COOH | H | CH₃ | H | 200 | 5 hours Δ = 118 |
| | | | | | 8 hours Δ = 69 |
| | | | | | 24 hours Δ = 44 |
| COOC₂H₅ | H | CH₃ | C₂H₅ | 200 | 3 hours Δ = 82 |
| | | | | | 5 hours Δ = 144 |
| | | | | | 8 hours Δ = 107 |
| | | | | | 24 hours Δ = 80 |

I claim:

1. An imidazo (2,1-b) thiazole compound having the formula:

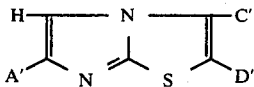

in which;

A' is COOR" or CH₂OCOR'", wherein R" is hydrogen, H₃N+C(CH₂OH)₃, H₃N+C(CH₃)₂CH₂OH, HN+(CH₂CH₂OH)₃, HN+(CH₂CH₃)₃, a pharmaceutically acceptable inorganic cation or a lower alkyl group; and R'" is an alkyl group containing one to eight carbon atoms or parachlorophenyl;

C' is methyl; and

D' is hydrogen or an alkyl group containing one to eight carbon atoms;

said compound being free of the 5-carbalkoxy isomer thereof; and physiologically acceptable acid addition or quaternary salts thereof.

2. An imidazo(2,1-b)thiazole according to claim 1 being 3-methyl-6-carbomethoxy-imidazo(2,1-b)thiazole.

3. An imidazo(2,1-b)thiazole having the formula 3-methyl-6-carbomethoxy-imidazo (2,1-b)thiazolium methyl iodide.

4. An imidazo(2,1-b)thiazole according to claim 1 being 3-methyl-imidazo(2,1-b)thiazole-6-carboxylic acid.

5. An imidazo(2,1-b)thiazole according to claim 1 being 3-methyl-6-carboethoxy-imidazo(2,1-b)thiazole.

6. An imidazo(2,1-b)thiazole according to claim 1 being 3-methyl-6-carbopropoxy-imidazo(2,1-b)thiazole.

7. An imidazo(2,1-b)thiazole according to claim 1 being 3-methyl-6-carboisopropoxy-imidazo(2,1-b)thiazole.

8. An imidazo(2,1-b)thiazole according to claim 1 being 3-methyl-6-carbobutoxy-imidazo(2,1-b)thiazole.

9. An imidazo(2,1-b)thiazole according to claim 1 being 3-methyl-6-carboisobutoxy-imidazo(2,1-b)thiazole.

10. An imidazo(2,1-b)thiazole according to claim 1 being 3-methyl-6-sec.carbobutoxy-imidazo(2,1-b)thiazole.

11. An imidazo(2,1-b)thiazole according to claim 1 being 3-methyl-6-p-chlorobenzoyloxymethyl-imidazo(2,1-b)thiazole.

12. An imidazo(2,1-b)thiazole according to claim 1 being 2,3-dimethyl-6-carbomethoxy-imidazo(2,1-b)thiazole.

13. An imidazo(2,1-b)thiazole according to claim 1 being 2-ethyl-3-methyl-6-carbomethoxy-imidazo(2,1-b)thiazole.

14. An imidazo(2,1-b)thiazole according to claim 1 being 2-propyl-3-methyl-6-carboethoxy-imidazo(2,1-b)thiazole.

15. An imidazo(2,1-b)thiazole according to claim 1 being 2-butyl-3-methyl-6-carboethoxy-imidazo(2,1-b)thiazole.

16. An imidazo(2,1-b)thiazole according to claim 1 being 2-isoamyl-3-methyl-6-carboethoxy-imidazo(2,1-b)thiazole.

17. An imidazo(2,1-b)thiazole according to claim 1 being 2,3-dimethyl-imidazo(2,1-b)thiazole-6-carboxylic acid.

18. An imidazo(2,1-b)thiazole according to claim 1 being 2-ethyl-3-methyl-imidazo(2,1-b)thiazole-6-carboxylic acid.

19. An imidazo(2,1-b)thiazole according to claim 1 being 2,3-dimethyl-6-carboethoxy-imidazo(2,1-b)thiazole.

20. An imidazo(2,1-b)thiazole according to claim 1 being 2-ethyl-3-methyl-6-carboethoxy-imidazo(2,1-b)thiazole.

21. An imidazo(2,1-b)thiazole according to claim 1 being 2'-(hydroxymethyl)-1',3'-propanediol-2'-ammonium 3-methyl-imidazo(2,1-b)thiazole-6-carboxylate.

22. An imidazo(2,1-b)thiazole according to claim 1 being 2'-methyl-1'-propanol-2'-ammonium 3-methyl-imidazo (2,1-b)thiazole-6-carboxylate.

23. An imidazo(2,1-b)thiazole according to claim 1 being 2'-(hydroxymethyl)-1',3'-propanediol-2'-ammonium 2-ethyl-3-methyl-imidazo(2,1-b)thiazole-6-carboxylate.

24. An imidazo(2,1-b)thiazole according to claim 1 being triethanolammonium 2-ethyl-3-methyl-imidazo(2,1-b) thiazole-6-carboxylate.

25. An imidazo(2,1-b)thiazole according to claim 1 being triethylammonium 3-methyl-imidazo(2,1-b)thiazole-6-carboxylate.

26. An imidazo(2,1-b)thiazole, having the formula 3-t.butyl-6-carbomethoxy-imidazo(2,1-b)-thiazole.

27. An imidazo(2,1-b)thiazole, having the formula 3-phenyl-6-carbomethoxy-imidazo(2,1-b)thiazole.

* * * * *